United States Patent [19]

Eggerman

[11] Patent Number: 5,149,292

[45] Date of Patent: Sep. 22, 1992

[54] BEE NEST STRIPPER

[75] Inventor: Percy A. Eggerman, Watson, Canada

[73] Assignee: Eggerman Farms Ltd., Watson, Canada

[21] Appl. No.: 650,199

[22] Filed: Feb. 4, 1991

[30] Foreign Application Priority Data

Nov. 15, 1990 [CA] Canada ................................. 2030095

[51] Int. Cl.$^5$ .............................................. A01K 51/00
[52] U.S. Cl. .......................................... 449/1; 449/56; 449/61
[58] Field of Search .................... 449/1, 4, 52, 56, 61; 15/104.02, 104.05, 104.011, 104.012

[56] References Cited

U.S. PATENT DOCUMENTS 1,458,691  6/1923  Elwell ............................. 15/104.011
5,035,796  7/1991  Saylor et al. ................. 15/104.05 X

FOREIGN PATENT DOCUMENTS

3025542  1/1982  Fed. Rep. of Germany ........ 449/61
707552  1/1980  U.S.S.R. ................................. 449/61

Primary Examiner—Robert P. Swiatek
Attorney, Agent, or Firm—Murray E. Thrift; Stanley G. Ade; Adrian D. Battison

[57] ABSTRACT

A hole in a leafcutter bee nest is stripped by pushing a thin tube into the hole to separate larvae in the hole from the surrounding nest material. An ejector, for example a rod sliding in the tube, is used to eject the separated larvae and cocoons. The method is carried out using an apparatus with foot guides for engaging a nesting block and aligning the tubes with a row of holes in the block, and a sequential drive. The drive first pushes the tubes through the block then drives the rods through the tubes. The tubes and rods are then withdrawn. The foot guide is subsequently lifted out of engagement with the nesting block and the block is indexed one hole forwards for stripping of the next row of holes.

19 Claims, 7 Drawing Sheets

BEE NEST STRIPPER

FIELD OF THE INVENTION

The present invention relates to the harvesting of leafcutter bee larvae from nest blocks and more particularly to a novel method and apparatus for this purpose.

BACKGROUND

Leafcutter bees in the larval stage reside in holes of approximately six millimeters diameter, one hundred millimeter depth in a nesting block. The block is typically a rectangular prism of synthetic foam with several hundred holes arranged in rows and columns. Typically, about ten larvae pupate end to end in a hole. They are harvested by removing them from the hole and are subsequently grown to the adult stage for use in pollinating crops.

The current method of removing the larvae from the nest blocks is simply to push a rod through the hole, forcing out all of the contents of the hole. This is usually done with a mechanical contrivance. This method of ejection has proven too brutal as it causes some of the larvae to be crushed.

The present invention aims at the provision a method and apparatus for removing the larvae from nest blocks more gently than was the case with the prior art.

SUMMARY

According to one aspect of the present invention there is provided a method of stripping larvae from a hole through a leafcutter bee nest, said method comprising:

extending into the hole a tube having a close fit in the hole and thereby separating larvae from the nest around the hole; and ejecting the larvae from the hole.

The tube, when pressed into the hole, separates the larvae and their cocoons from the sides of the hole, and the cocoons and larvae pass into the tube. Subsequently, the pupating larvae may be ejected against little resistance, so that no crushing damage occurs.

According to another aspect of the present invention there is provided a stripper for a leaf cutter bee nest having a hole therethrough, the stripper comprising:

a tube shaped and sized to fit closely into the hole in the nest;

tube driving means for driving the tube into the hole in the nest to separate larvae therein from the nest surrounding the hole; and ejection means for ejecting larvae from the hole.

The ejection means may be a rod sliding in the tube.

Preferably, the apparatus includes an alignment foot for engaging the nest block and aligning a row of tubes with a row of holes in the block for extraction of a hole at each operating stroke. A stepped drive indexes the movement of the nest block past the tubes and ejection rods.

It is known that the cocoon structure differs from the inner end of the hole to the outer. In the outer approximately one-third of the hole, the cocoon adheres much more strongly to the nest. To ensure that this portion of the cocoon is separated from the hole, regardless of which side of the nest the tube enters, it is preferred that the tube extend through the hole from side to side.

BRIEF DESCRIPTION OF THE DRAWINGS

In the accompanying drawings, which illustrate an exemplary embodiment of the present invention.

DETAILED DESCRIPTION

Figure 1:
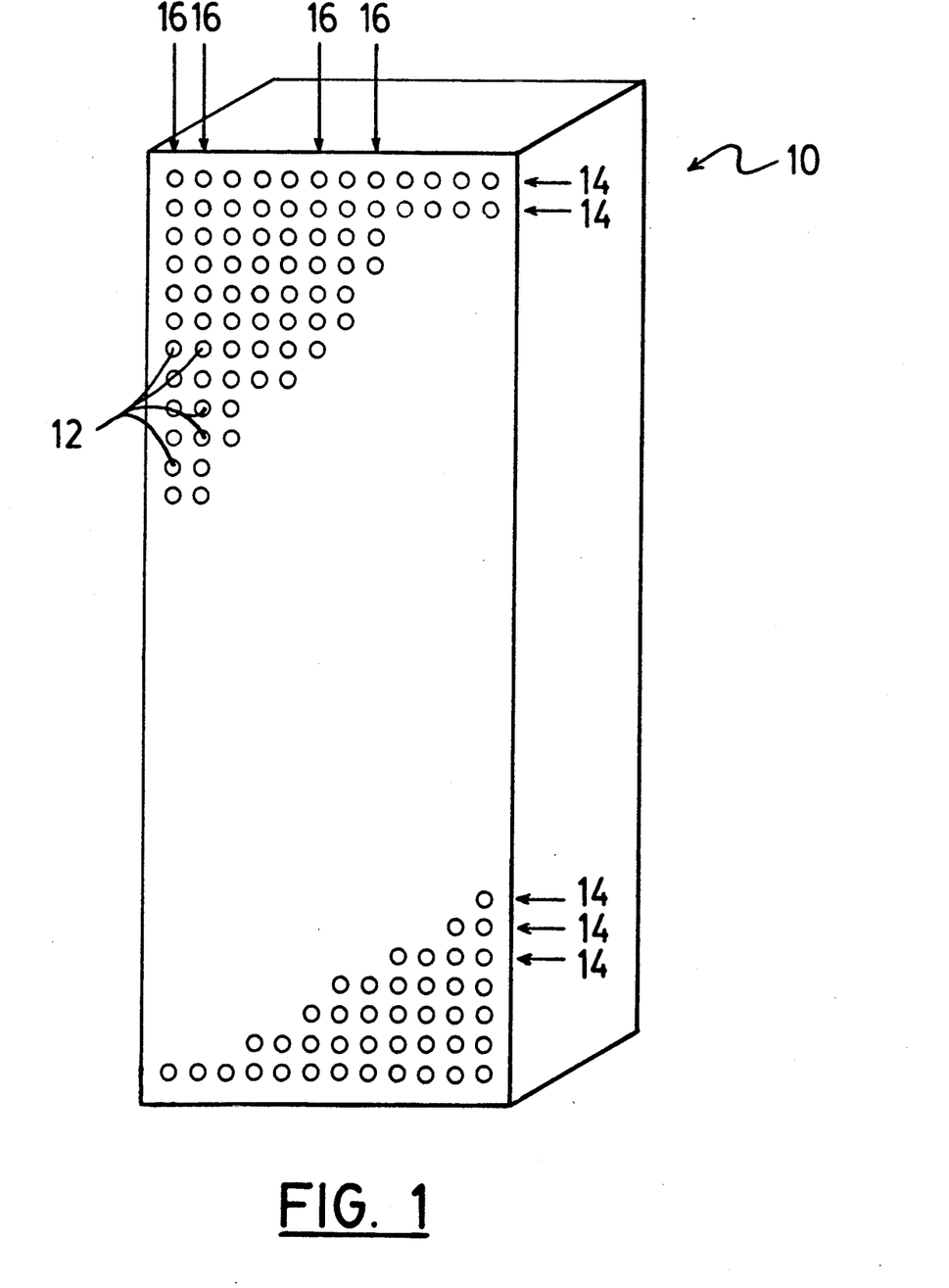
FIG. 1 is an isometric view of a nest block.

Referring to the accompanying drawings, and especially to FIG. 1, a leaf cutter bee nest block 10 is a rectangular prism of synthetic foam with a large number of through holes 12 arranged in rows 14 and columns 16. The bee larvae pupate in the holes in the nest block, with an average of ten larvae occupying each hole. The larvae are to be stripped from the holes without significant damage to the larvae.

Figure 2:
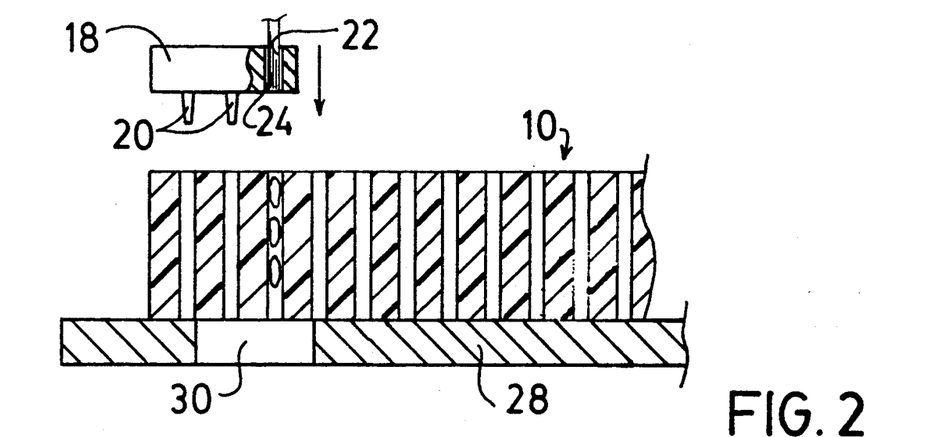
FIGS. 2, 3, and 4 are schematic views showing the sequence of an extraction operation.
Figure 3:
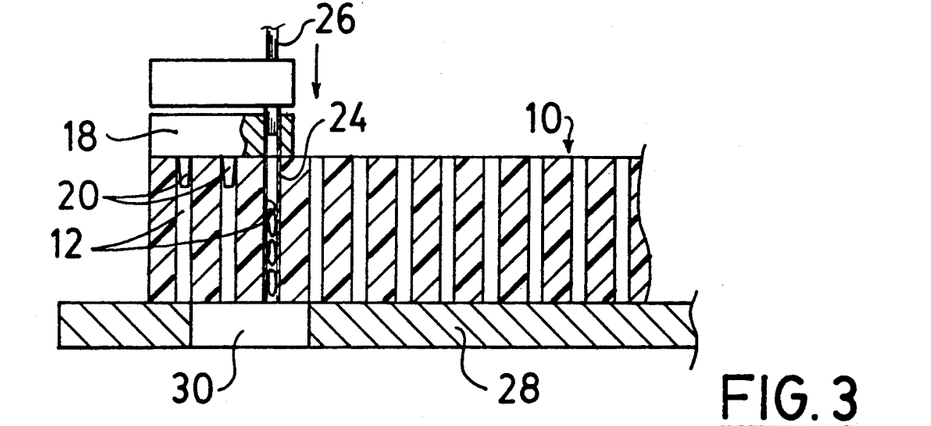
Figure 4:
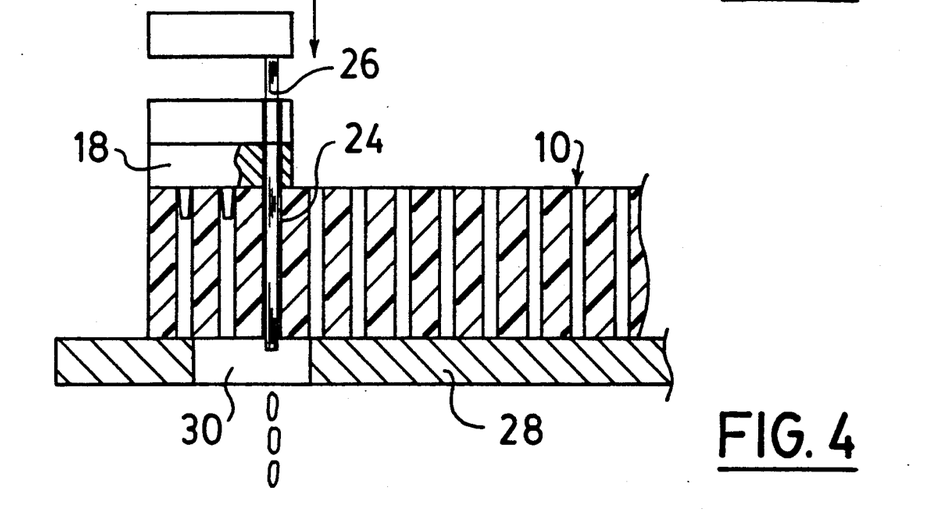
Figure 5:
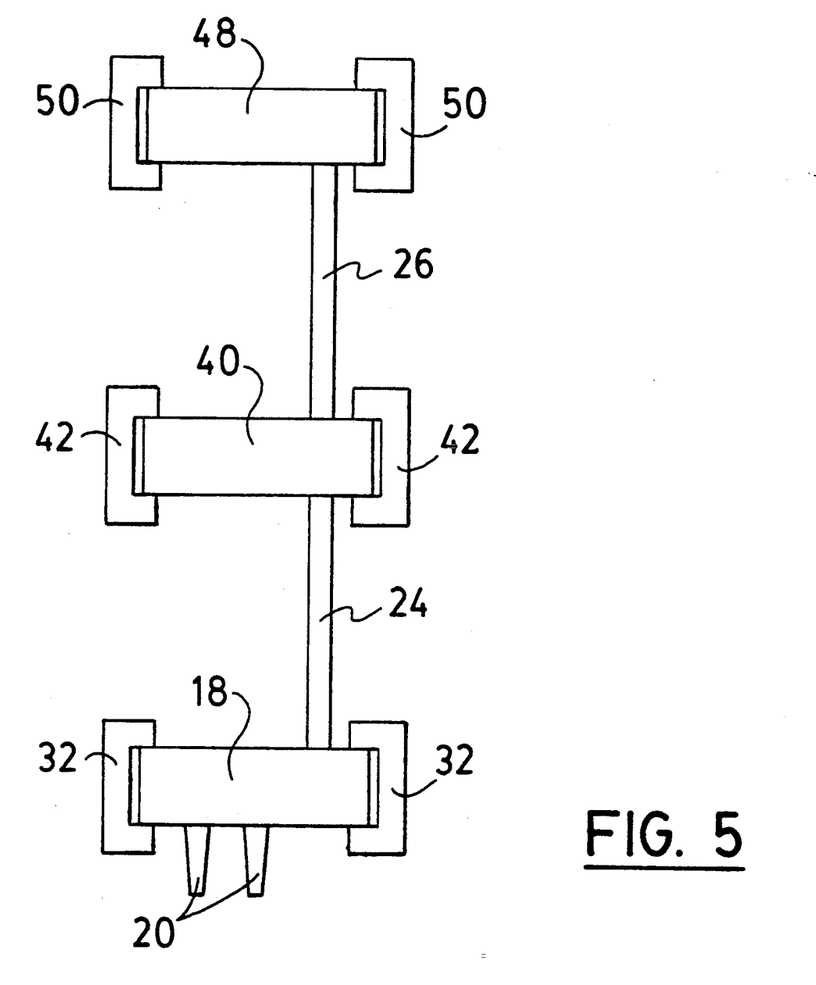
FIG. 5 is a schematic side elevation showing the extraction components of the apparatus.
Figure 6:
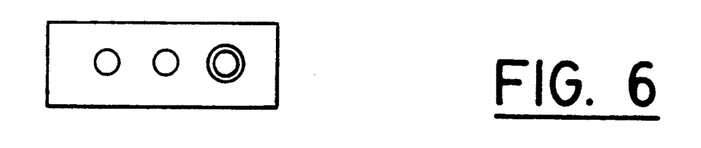
FIG. 6 is a plan view of a foot guide.
Figure 7:
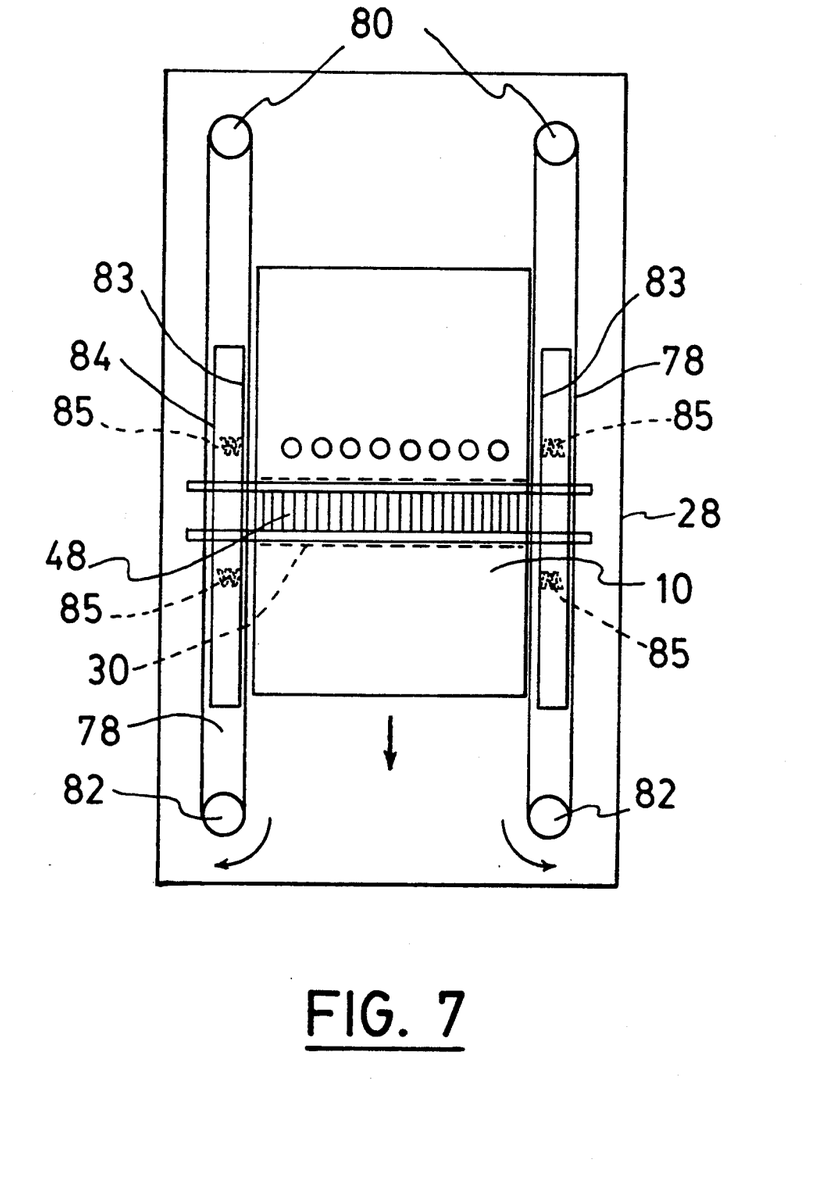
FIG. 7 is a plan view of the overall apparatus.
Figure 8:
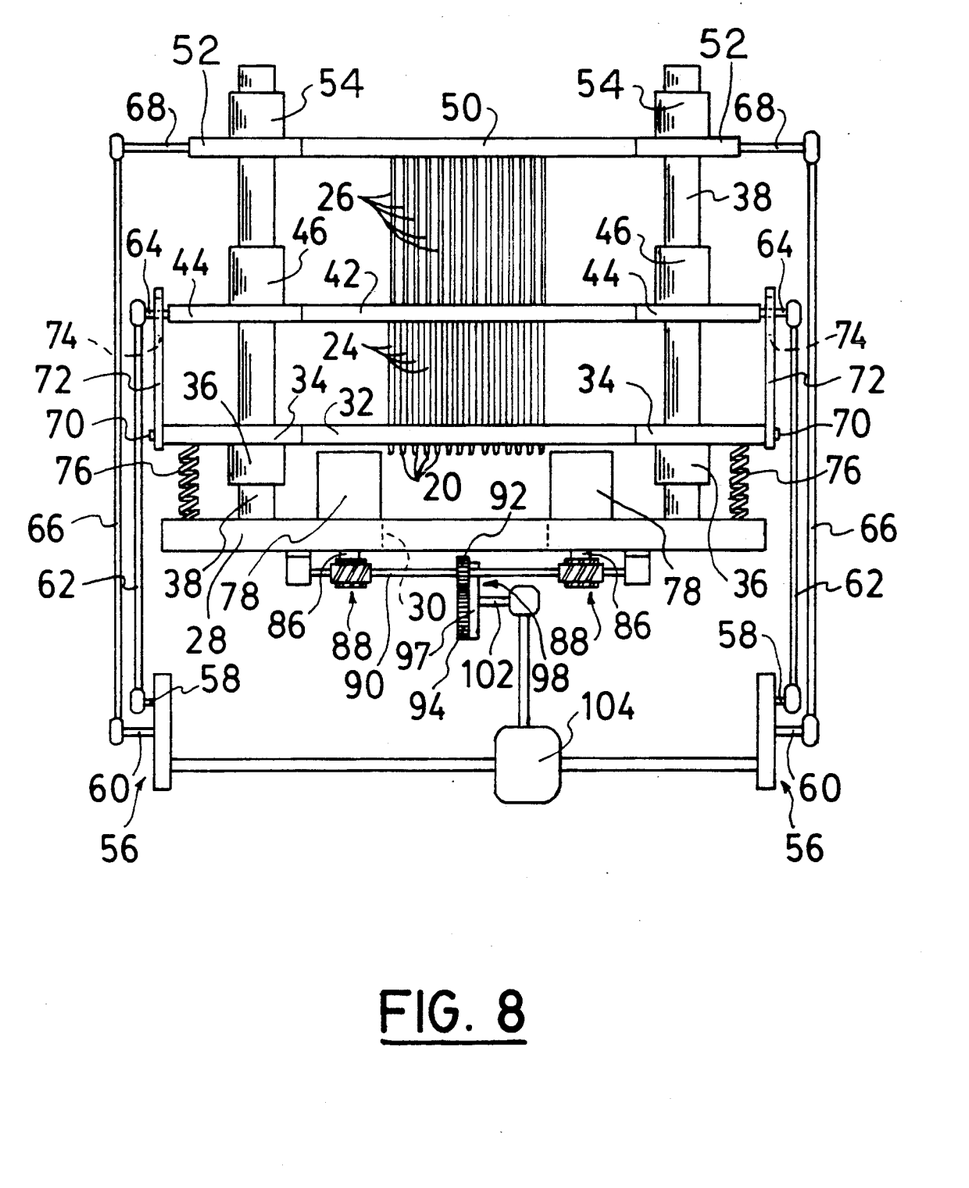
FIG. 8 is an end elevation of the apparatus.
Figure 9:
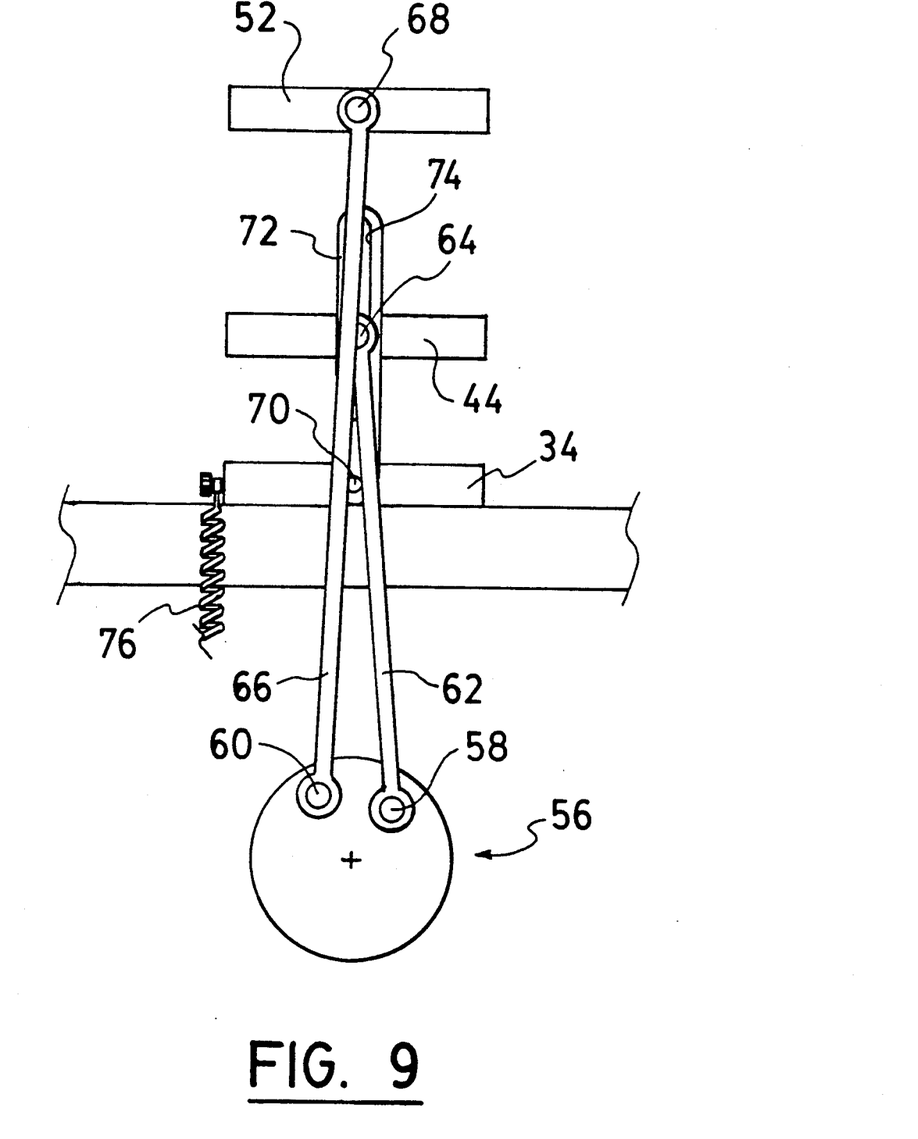
FIG. 9 is a side elevation of a drive mechanism.

FIGS. 2, 3, and 4 illustrate schematically the steps for extracting bees from nest blocks. As illustrated in FIG. 2 a foot guide 18 is positioned above the block. The guide has two tapered pins 20 projecting from the lower face. A tube guide hole 22 extends vertically through the foot guide and receives slidably therein a thin tube 24. The tube has a typical wall thickness of between 0.1 and 0.2 millimeters. A rigid rod 26 slides in the tube 24. In the inital position illustrated in FIG. 2, the foot guide 18 is lowered into engagement with the top of the nest block 10. The tapered pins 20 engage in adjacent holes 12 in the nest block to ensure alignment of the tube guide hole 22 with the next following hole 12. In the next step, iullustrated in FIG. 3, the tube 24 is pushed through the hole 12 with which it is aligned. The contents of the hole are separated from the nest material surrounding the hole and enter the tube 24.

The next step in the method, as illustrated in FIG. 4 is the extension of rod 26 through the tube 24 to eject the contents of the tube. It has been found that this method of first separating larvae from the nest block material and then ejecting the larvae from the tube to which they have no connection eliminates the high frictional forces encountered in the previous method, which results in crushing of the larvae. After the ejection of the larvae from the tube, the tube is withdrawn from the nesting block hole, the rod is withdrawn from the tube and the foot guide 18 is lifted to draw the tapered pins 20 from engagement with the nesting block. The block is then be indexed one hole forward for a repetition of the procedure.

The method illustrated schematically in FIGS. 2, 3 and 4 is carried out automatically, in a stepwise manner, row by row using an apparatus as illustrated in FIGS. 5 through 9. As illustrated, the apparatus has a support bed 28 on which the nest block is supported for stripping. In the centre of the bed is a transverse opening 30 through which the block contents can be discharged for collection.

The foot guides are independent rectanguular blocks arranged side by side across the bed of the apparatus with one foot guide for each column of holes in the nest block. The guides are seated loosely in two lateral channels 32 so that they can move freely, within limits, over the bed. This arrangement, in conjunction with guide pins 20 with a taper of about one in three allows the pins to engage the holes in the nest block even if the nest block and foot guide are out of alignment by as much as say three to four millimeters.

The channels 32 are secured together at their opposite ends by connector bars 34 that project beyond the ends of the channels 32 and carry large bushings 36 engaged slidably on respective vertical columns 38 on opposite sides of the bed. The columns thus guide the entire foot guide assembly for vertical movement during operation of the apparatus.

Each of the tubes 24 is connected to a tube holder 40 in the form of a rectangular block. Like the foot guides, the tube holders are arranged side by side across the apparatus and are retained in a pair of tube holder channels 42 fixed together by connector bars 44 at the opposite end. The connector bars project beyond the ends of the channels 42 and carry bushings 46 to engage on the respective columns 38.

Rods 26 are individually connected to rod holders 48 in the form of rectangular blocks arranged side by side across the apparatus and held in place by rod holder channels 50 coupled by connector bars 52. The rod holder connector bars carry respective bushings 54 that engage slideably on the columns 38.

Vertical movements of the foot guides 18, the tubes 24 and the rods 26 are controlled by two symmetrically arranged crank mechanisms, one on either side of the apparatus. Each crank 56 includes two throws 58 and 60 spaced 45° from one another. The connecting rod 62 is connected to the leading throw 58 and to a wrist 64 on the adjacent tube holder connector bar 44. A connecting rod 66 is coupled to the trailing throw 60 and to a wrist pin 68 on the rod holder connector bars 52.

The foot guides are not operated directly by crank but rather indirectly through the motion of the tube holders. The connector bars of the foot guide assembly have pins 70 projecting from their ends, carrying respective lift links 72. The lift links have elongate slots 74 engaging over the wrist pins 64 of the tube holder assembly. The foot guide assembly is biased to a lowered position by hold down springs 76 connected to the foot guide connector bars.

In operation, rotation of the crank 56 causes the wrist pins 64 to engage the top of the slot 74 to lift the guide assembly so that the pins 20 are clear of the holes in the nest block. Continued rotation of the crank to turn the throw 50 beyond top dead centre begins to lower the foot guide assembly to allow the pins 20 to engage holes in a nesting block supported on the bed 28 of the apparatus. The hold down springs pull the foot guide snugly down until the tapered pins are in a tight fit with the associated holes of the nesting block. At this time, the tube guide holes 22 in the foot guides are in alignment with the holes 12 of the nest block immediately following the foot guide pins 20. The continued rotation of the crank 56 lowers the tubes through the foot guide holes and the holes in the nesting block. Following this movement, 45° out of phase, is a similar movement of the rods 26 through the tubes 24.

The nesting blocks are advanced along the bed, past the stripping station by a pair of opposed timing belts 78 engaging opposite sides of the block. Each belt runs over an idler sprocket 80 at one end of the bed and drive sprocket 82 at the other. Between the two sprockets are backing plates 83 mounted on support blocks 84 by bias springs 85. These force the belts into engagement with the opposite sides of the nesting block.

Figure 10:
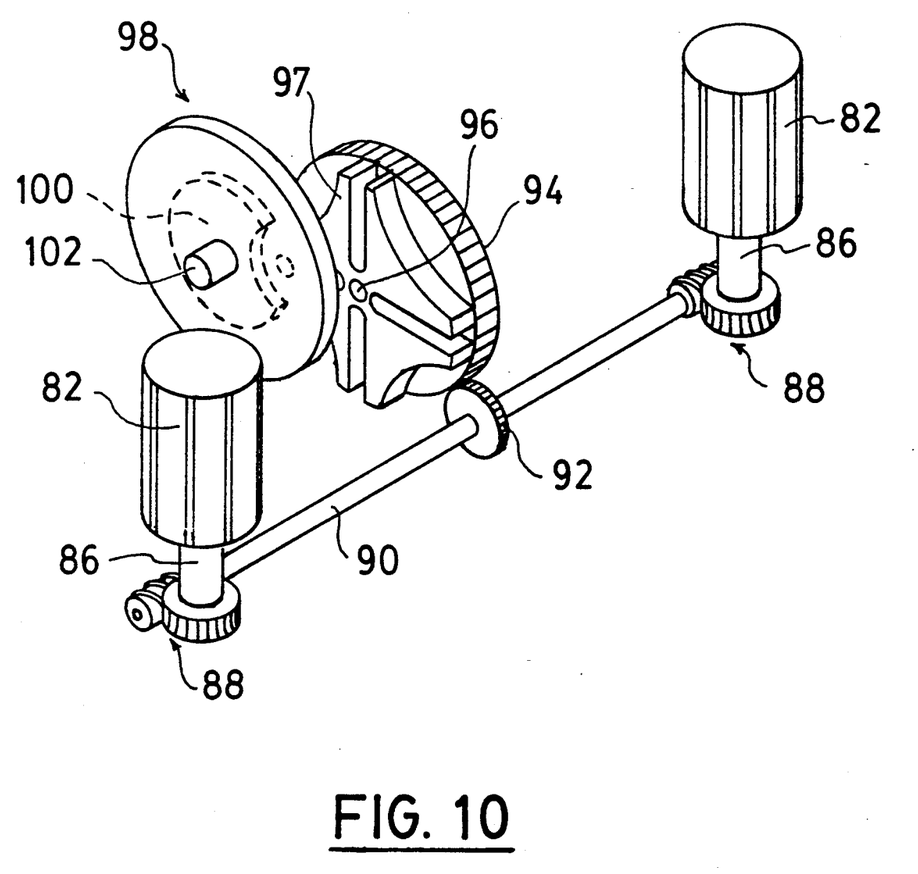
FIG. 10 is an isometric of an intermittent drive for the apparatus.

Each of the drive sprockets 82 has a drive shaft 86 that extends through the bed of the stripper for connection to a worm gear reducer 88. The two worm gear reducers are connected by a cross shaft 90 driven by a gear 92 from a drive gear 94. Gear 94 is mounted on a common shaft 96 with the indexing wheel 97 of a geneva wheel mechanism 98. The rotor 100 of the geneva wheel mechanism is mounted on a shaft 102 driven continuously from an electric motor 104 that also supplies power for the crank 56.

In operation of the apparatus, the rotation of the crank 56 acts, through the connecting rod 62 and the wrist pin 64 to lift the foot guide and its tapered pins 20 out of engagement with the nesting block. As the wrist pin 64 reaches top dead centre, the geneva wheel engages to index the timing belts forwards by one step, thus advancing the nest block past the stripping station a distance equal to the spacing between two adjacent rows of holes. The geneva wheel then enters an idle phase, holding the nesting block in position, while the crank continues to rotate, lowering the wrist pin 64 and allowing the foot guide pins 20 to engage holes in the nesting block to align the tub guide holes 22 with the next following nest block hole. The tubes are then drawn down into the holes in the nesting blocks, followed, at a 45° phase lag, by the rods 26 descending through the tubes. At the bottom dead centre position of crank throw 58, the tubes 24 begin to rise out of the block, while the rods 26 continue to descend, driving all collected material out of the tubes and through the opening 30 in the bed. The tubes and pins are withdrawn as the crank continues to rotate, with the elevation of the tubes drawing the foot guide 18 upwardly through the action of the wrist pin 64 on the lifting links 72. The block is then indexed once more and the complete stripping cycle repeated.

The foot guides, the tube holders and the rod holders are held within their respective channels with a clearance fit of 0.25 to 0.5 millimeters. This allows the stripping components to move slightly so that the points of the tapered pins 20 will enter the intended holes in the nest blocks even if they are three to four millimeters out of alignment.

While one embodiment of the present invention has been described in the foregoing, it is to be understood that other embodiments are possible within the scope of the invention. For example, the driving mechanism for sequentially inserting the guide pins, the tubes and the ejection rods may be configured as two slider-crank mechanisms rather than a crank and connecting rod arrangement. The intermittent feed may be produced by mechanisms other than the geneva wheel illustrated, for example, an indexing wheel driven by an indexing pin on a rotor. Non-mechanical systems will also be apparent to those knowledgeable in the art.

It is also possible to use a shorter tube in order to separate only the outer one-third to one-half of the hole contents from the next block, although this is not considered to be as satisfactory. A separate ejector, not sliding in the tube, is also possible. In the past attempts have been made to use an air blast for stripping nests. This has not proven satisfactory, but may prove useful as an ejection means in conjunction with the separating tube. The invention is therefore to be considered limited solely by the scope of the appended claims.

I claim:

1. A method of stripping larvae from a hole through a leaf cutter bee nest, said method comprising:
   extending into the hole a tube having a close fit in the hole and thereby separating larvae from the nest around the hole; and
   ejecting the larvae from the hole.

2. A method according to claim 1 comprising extending the tube through the hole.

3. A method according to claim 1 comprising ejecting the larvae by extending a rod through the tube.

4. A method of stripping larvae from a leafcutter bee nest having at least one row of holes therethrough, the method comprising:
   extending substantially simultaneously through a plurality of the holes, respective ones of a plurality of tubes each having a close fit in the respective hole and thereby separating larvae from the nest around the hole; and
   subsequently simultaneously extending a plurality of rods through respective ones of the tubes.

5. A method according to claim 4 wherein the nest comprises a nest block with a plurality of holes therethrough, arranged in rows and columns, said method comprising:
   a) aligning the holes of a first row of the holes with respective ones of the tubes;
   b) extending the tubes simultaneously through the holes aligned therewith;
   c) extending the rods simultaneously through respective ones of the tubes;
   d) withdrawing the rods from the tubes and the tubes from the holes;
   e) moving the nest block relative to the tubes to align the holes of a subsequent row of holes with respective ones of the tubes; and
   f) repeating steps b) to e) for each subsequent row of holes.

6. A stripper for a leaf cutter bee nest having at least one row of holes therethrough, the stripper comprising:
   a plurality of tubes corresponding in number and spacing to the holes in said at least one row of holes, each tube being shaped and sized to fit closely into a hole in the nest;
   tube driving means for driving the tubes into respective ones of the holes in the nest to separate larvae therein from the nest surrounding the holes; and
   ejection means for ejecting larvae from the holes.

7. Apparatus according to claim 6 wherein the ejection means comprise a plurality of ejection rods corresponding to respective ones of the tubes.

8. Apparatus according to claim 7 wherein each ejection rod is shaped and sized to fit closely into the associated tube.

9. Apparatus according to claim 8 wherein the ejection means further comprises rod driving means for driving the rods through the tubes.

10. Apparatus according to claim 9 wherein the nest block comprises plural rows of holes arranged in sequence and the stripper includes block advancing means for moving the nest block stepwise relative to the tubes to bring the sequential rows of holes into alignment with the tubes.

11. Apparatus according to claim 10 wherein the tube driving means comprise means for driving the tubes simultaneously through the respective holes of a row and the rod driving means comprise means for driving the rods simultaneously through the respective tubes.

12. Apparatus according to claim 11 wherein the block advancing means comprise timing belts for engaging opposite sides of a nest block and means for driving the timing belts.

13. Apparatus according to claim 12 wherein the means for driving the timing belts comprise a geneva wheel intermittent drive.

14. Apparatus according to claim 14 including alignment means for aligning the tubes with the respective holes of a row of holes.

15. Apparatus according to claim 14 wherein the alignment means comprise a foot engaged with the tubes, alignment pins on the foot, and foot setting means for moving the alignment pins relative to a nest block for engaging the alignment pins with respective holes in the nest block.

16. Apparatus according to claim 15 wherein the alignment means include mounting means mounting the tubes and the ejection rods for movement together with the alignment pins whereby the tubes and ejection rods may be brought into alignment with the holes of a selected row in response to engagement of the alignment pins with respective holes in the nest block.

17. Apparatus according to claim 16 wherein the alignment pins are tapered.

18. Apparatus according to claim 17 wherein the mounting means include tube holder carrying the tube, rod holder means carrying the ejection rods and support means supporting the tube and rod holder means and the foot for limited free movement laterally of the holes.

19. Apparatus according to claim 18 wherein the support means comprise channels engaged with opposite edges of each tube and rod holder means.

* * * * *